US00PP35504P2

(12) United States Plant Patent
Lim

(10) Patent No.: US PP35,504 P2
(45) Date of Patent: Nov. 28, 2023

(54) FLORIBUNDA SHRUB ROSE PLANT NAMED 'ALTCHILLI'

(50) Latin Name: *Rosa hybrida*
Varietal Denomination: ALTchilli

(71) Applicant: Peter Lim, Escondido, CA (US)

(72) Inventor: Peter Lim, Escondido, CA (US)

(73) Assignee: Altman Specialty Plants Inc, Vista, CA (US)

( * ) Notice: Subject to any disclaimer, the term of this patent is extended or adjusted under 35 U.S.C. 154(b) by 0 days.

(21) Appl. No.: 18/091,684

(22) Filed: Dec. 30, 2022

(51) Int. Cl.
*A01H 5/02* (2018.01)
*A01H 6/74* (2018.01)

(52) U.S. Cl.
USPC ..... Plt./108

(58) Field of Classification Search
USPC ..... Plt./108, 150, 151, 140
CPC ... A01H 5/02; A01H 5/00; A01H 6/74; A01H 6/749
See application file for complete search history.

(56) References Cited

U.S. PATENT DOCUMENTS

PP5,105 P * 9/1983 Meilland ..... Plt./107
PP5,519 P * 7/1985 McGredy, IV ..... Plt./139

OTHER PUBLICATIONS

Help Me Find Roses, Clematis and Peonies, retrieved on Mar. 28, 2023 at https://www.helpmefind.com/rose/pl.php?n=11752, one page. (Year: 2023).*
Sooner Plant Farm, retrieved on Mar. 27, 2023 at https://www.soonerplantfarm.com/plant/rose-easy-elegance-kashmir, 7 pp. (Year: 2023).*

* cited by examiner

*Primary Examiner* — June Hwu
(74) *Attorney, Agent, or Firm* — Cassandra Bright

(57) ABSTRACT

A new and distinct cultivar of *Rosa* plant named 'ALTchilli' is disclosed, characterized by distinctive fully double dark red flowers with a tea rose fragrance. Plants are vigorous and can be grown on their own roots. Plants flower early and continuously, and exhibit good resistance to blackspot disease. The new variety is a *Rosa*, normally produced as an outdoor garden or container plant.

1 Drawing Sheet

Latin name of the genus and species: *Rosa hybrida.*
Variety denomination: 'ALTchilli'.

BACKGROUND OF THE INVENTION

The new *Rosa* cultivar is a product of a planned breeding program conducted by the inventor, Peter Ping Lim. The objective of the breeding program was to produce vigorous new garden rose varieties with continuous blooming for ornamental commercial applications. The cross resulting in this new variety was made during June of 2014.

The seed parent is the variety *Rosa* 'Baigirl', U.S. Plant Pat. No. 19,952. The pollen parent is the variety *Rosa* 'Crimson Glory', U.S. Plant Pat. No. 105. The new variety was selected in July of 2015 by the inventor in a group of seedlings resulting from the 2014 crossing, in a nursery in Vista, Calif.

Asexual reproduction of the new cultivar has been performed by vegetative cuttings. This was first performed at a research greenhouse in Vista, Calif. in July of 2015 and has shown that the unique features of this cultivar are stable and reproduced true to type in more than 5 successive generations.

SUMMARY OF THE INVENTION

The cultivar 'ALTchilli' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'ALTchilli' These characteristics in combination distinguish 'ALTchilli' as a new and distinct *Rosa* cultivar:

1. Double flower with more than 50 petals.
2. Dark red flower color.
3. Flower form and color are different than both parents.
4. Early blooming.
5. Dark glossy foliage resistant to black spot (*Diplocarpon rosae*) and powdery mildew (*Podosphaera pannosa*) disease.
6. Plants can be grown on their own roots; grafting is not required.

PARENT COMPARISONS

Plants of the new cultivar 'ALTchilli' are similar to plants of the seed parent, in most horticultural characteristics, however, plants of the new cultivar 'ALTchilli' differ in the following:

1. Flowers of the new cultivar are dark red, while flowers of the seed parent are pink.
2. Petal count of the new variety is higher than petal count of this parent.
3. Plant size of the new variety is smaller than plant size of this parent.

Plants of the new cultivar 'ALTchilli' are similar to plants of the pollen parent in most horticultural characteristics, however, plants of the new cultivar 'ALTchilli' differs in the following;

1. The new variety has more petals than the pollen parent.
2. The new variety is a smaller plant than the pollen parent.
3. The new variety can be grown on its own roots; the pollen parent must be grafted.

COMMERCIAL COMPARISONS

Plants of the new cultivar 'ALTchilli' can be compared to the commercial variety *Rosa* 'Meidomonac', U.S. Plant Pat. No. 5,105. These varieties are similar in most horticultural characteristics, however 'ALTchilli' differs in the following:

1. Flowers of the new variety produce more petals than this comparator.
2. Flowers of the new variety have a tea rose fragrance, while flowers of this comparator have no noticeable fragrance.
3. The new variety is a smaller plant than this comparator.

Plants of the new cultivar 'ALTchilli' can also be compared to the commercial variety *Rosa* 'MACauck', U.S. Plant Pat. No. 5,519. These varieties are similar in most horticultural characteristics, however 'ALTchilli' differs in the following:

1. Flowers of the new variety have more petals than this comparator.
2. Flowers of the new variety are a darker red color than flowers of this comparator.
3. The new variety is a smaller plant than this comparator.

BRIEF DESCRIPTION OF THE PHOTOGRAPH

The accompanying photograph illustrates in full color a close up of an individual flower. The photograph was taken using conventional techniques and although colors may appear different from actual colors due to light reflectance it is as accurate as possible by conventional photographic techniques

DETAILED BOTANICAL DESCRIPTION

In the following description, color references are made to The Royal Horticultural Society Colour Chart 2007 except where general terms of ordinary dictionary significance are used. The following observations and measurements describe 'ALTchilli' plants grown outdoors, in Palm Desert, Calif. The growing temperature ranged from approximately 10° C. to 38° C. during the day and from approximately 5° C. to 22° C. during the night. Measurements were taken in September. General light conditions were very bright, normal sunlight. Measurements and numerical values represent averages of typical plant types.

Botanical classification: *Rosa* 'ALTchilli'.

Market classification: Floribunda shrub rose.

PROPAGATION

Time to initiate roots: About 15 days at approximately 20° C.

Time to produce a rooted cutting: About 35 days at approximately 20° C.

PLANT

Age of plant described: Approximately 1.5 years.

Growth habit: Compact.

Container size: 2 gallon.

Height: 40 cm.

Plant spread: 50 cm.

Rootstock: Own root.

Growth rate: Moderate.

Branching characteristics: Sympodial branching.

Length of primary lateral branches: Average range 12 to 22 cm.

Diameter of lateral branches: Approximately 5 mm to 7 mm.

Quantity branches: 6 to 8 main branches, moderate lateral branches, 10 to 20 lateral branches per main branch.

Branches-young wood:

*Diameter*.—Approximately 4 mm.

*Texture*.—Glabrous, very dense soft, short thorns. As branches mature thorns become less dense and sharp.

*Color*.—Near RHS Green 143B.

Branches-old wood:

*Diameter*.—Approximately 5 to 8 mm.

*Color*.—Near RHS Green 137A.

*Texture*.—Glabrous.

*Thorns*.—

*Approximately density/quantity of thorns*.—Young growth: Very dense, soft thorns which disappear with maturity. Approximately 1 mm in diameter and 2 to 3 mm long. Colored near RHS Greyed-Purple 185B. With some maturity thorns becomes less dense and sharp. Intermediate thorns moderately dense, about 3 to 4 mm long colored near Green 143D, flushed Greyed-Red 179A. Mature growth: Sparsely to moderately dense, apiculate thorns about 4 mm at base, 4 mm to 5 mm long. Colored near RHS Grey-Orange 174C. Weakly hooked.

FOLIAGE

Leaf:

*Arrangement*.—Alternate and compound.

*Quantity*.—Average 8 to 12 per main branch.

*Internode*.—Average range 2 cm to 4.5 cm.

*Average length*.—Approximately 10 to 11 cm.

*Average width*.—Approximately 7 to 9 cm.

Rachis:

*Average length*.—Approximately 4.0 cm.

*Average diameter*.—Approximately 2 mm.

*Color*.—Upper surface: Near RHS Green 137B. Lower surface: Near RHS Green 143B.

*Texture*.—Glabrous all surfaces.

Leaflet:

*Quantity*.—5 or 7 per leaf, most commonly 5.

*Average length terminal leaflet*.—Approximately 5 cm to 6 cm.

*Average width terminal leaflet*.—Approximately 3.8 cm.

*Shape of blade*.—Broad ovate.

*Apex*.—Acute to somewhat mucronate.

*Base*.—Broadly rounded.

*Margin*.—Finely serrate. Very weakly undulate.

*Appearance of top surface*.—Glossy.

*Appearance of bottom surface*.—Matte.

*Texture of top surface*.—Glabrous.
*Texture of bottom surface*.—Glabrous.
*Color*.—Young foliage upper side: Near RHS 137B lightly flushed Greyed-Purple 183C along margin. Young foliage under side: Near RHS Green 138A, faintly flushed Greyed-Purple 183D. Mature foliage upper side: Near RHS Green 139A. Mature foliage under side: Near RHS Green 138A.
*Venation*.—Type: Reticulate. Venation color upper side: Near RHS Greyed-Purple 187B. Venation color under side: Near RHS Green 138B.

Petiole:
*Average length*.—Approximately 1.5 cm to 3.0 cm.
*Average diameter*.—Approximately 3 mm.
*Color*.—Upper surface: Near RHS Green 143C. Lower surface: Near RHS Green 143C.
*Petiole wing*.—Typically 18 mm long and 8 mm wide. Apex apiculate. Upper surface colored near RHS Green 137C, lower surface colored near Green 143B.
*Texture*.—Glabrous.

FLOWER

Natural flowering season: Spring until Autumn.
Inflorescence type and habit: Singly occurring fully double rotate flowers.
Rate of flower opening: Approximately 7 days from bud to fully opened flower.
Flower longevity on plant: About 10 to 14 days, after fully opened.
Quantity of flowers: 20 to 30 fully opened flowers and buds.
Flower size:
*Diameter*.—Approximately 7.5 cm.
*Height*.—Approximately 3.0 cm.
Flower shape:
*From above*.—Round.
*Profile of upper part of flower*.—Convex.
*Profile of lower part of flower*.—Flattened convex.
Peduncle:
*Length*.—3.0 cm to 5.0 cm.
*Diameter*.—3 mm.
*Color*.—Near RHS Green 143C lightly flushed Greyed-Purple 183B.
*Texture*.—Softly prickly.
Petals:
*Petal arrangement*.—Multiple rotate, overlapping whorls.
*Petal quantity*.—Average 50 to 65.
*Length*.—3.0 cm.
*Width*.—2.5 cm.
*Shape*.—Obovate.
*Margin*.—Entire. Moderately ruffled. Reflexing absent.
*Apex*.—Rounded.
*Base*.—Very broad attenuate.
*Texture*.—Glabrous all surfaces.
*Color*.—When opening: Upper surface: Near RHS Red 53A. Very small basal blotch near White N155C. Lower surface: Near RHS Red 53B. Very small basal blotch near White N155C. Fully opened. Upper surface: Near RHS Red 46A. Very small basal blotch near White N155C. Lower surface: Near RHS Red 53B. Very small basal blotch near White N155C.

Bud:
*Shape*.—Ovate.
*Length*.—Approximately 3.2 cm.
*Diameter*.—Approximately 1.8 cm.
*Color*.—Near RHS Red 53A.

Sepals:
*Quantity*.—5.
*Length*.—2.0 cm.
*Width*.—7 mm.
*Shape*.—Deltoid.
*Apex*.—Acute to slightly apiculate.
*Sepal extensions*.—Absent.
*Margin*.—Entire.
*Texture*.—Pubescent upper surface, glabrous lower surface.
*Color*.—Interior Surface: Near RHS Green 138B. Exterior Surface: Near RHS Green 138A.

Receptacle:
*Length*.—9 mm.
*Width*.—14 mm.
*Shape*.—Flat.
*Color*.—Near RHS Green 143C.

Fragrance: Moderate tea rose scent.

REPRODUCTIVE ORGANS

Stamens:
*Quantity*.—About 50.
*Filament length*.—Approximately 4 mm to 5 mm.
*Filament color*.—Near RHS White 155D.

Anthers:
*Length*.—2 mm.
*Shape*.—Narrow globular.
*Color*.—Near RHS Greyed-Orange 167A.
*Pollen*.—Color: Near RHS Greyed-Orange 167B. Quantity: Scant or none.

Pistil: Not observed.

OTHER CHARACTERISTICS

Seeds and fruits: Not observed.
Disease/pest resistance: Good overall disease resistance to normal pests and diseases typical of garden roses. Very good resistance to blacks pot (*Diplocarpon rosae*). Very good resistance to powdery mildew (*Podosphaera pannosa*). In a three-year confidential field trial of floribunda shrub roses the new variety 'ALTchilli' remains free of powdery mildew year-round while varieties planted nearby were showed symptoms of powdery mildew.

What is claimed is:

1. A new and distinct floribunda shrub rose plant named 'ALTchilli' as herein illustrated and described.

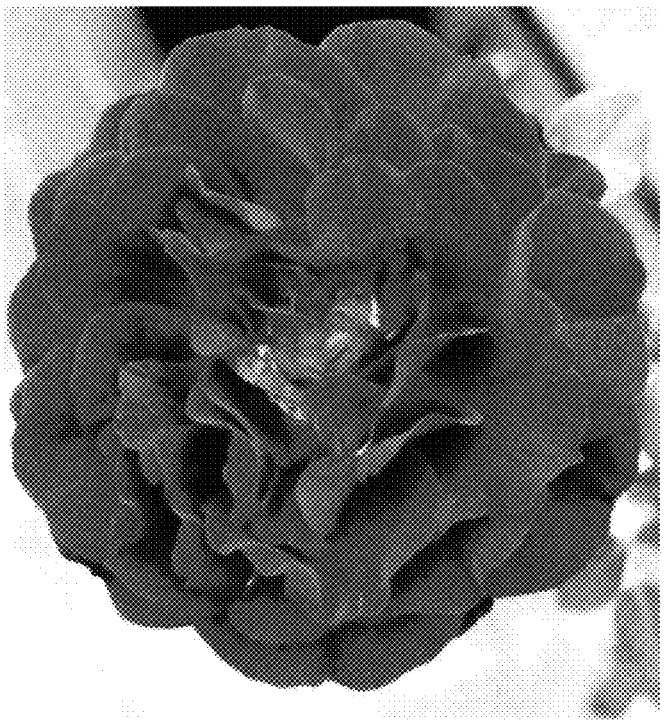

* * * * *